United States Patent [19]

Pallin

[11] Patent Number: 5,080,111
[45] Date of Patent: Jan. 14, 1992

[54] METHOD OF MAKING SELF-SEALING EPISCLERAL INCISION

[76] Inventor: Samuel L. Pallin, 10615 W. Thunderbird Blvd., Sun City, Ariz. 85351

[21] Appl. No.: 544,984

[22] Filed: Jun. 28, 1990

[51] Int. Cl.$^5$ .............................................. A61F 9/00
[52] U.S. Cl. .................................. 128/898; 606/107
[58] Field of Search ................ 606/107, 161, 166; 128/898; 623/6

[56] References Cited

U.S. PATENT DOCUMENTS

| | | | |
|---|---|---|---|
| 4,607,617 | 8/1986 | Choyce | 606/107 |
| 4,619,657 | 10/1986 | Keates et al. | 606/107 |
| 4,702,244 | 10/1987 | Mazzocco | 606/107 |
| 4,706,666 | 11/1987 | Sheets | 606/107 |
| 4,773,415 | 9/1988 | Tan | 606/107 |
| 4,844,065 | 7/1989 | Faulkner | 606/107 |
| 4,959,070 | 9/1990 | McDonald | 606/107 |

Primary Examiner—John D. Yasko
Assistant Examiner—William Lewis
Attorney, Agent, or Firm—Harry A. Wolin

[57] ABSTRACT

A substantially self-sealing episcleral incision having an approximate central point 1.5 to 3.0 millimeters posterior to the limbus. Portions of the incision extending from the approximate central point extend laterally away from the curvature of the limbus. The configuration of the self-sealing incision allows the incision to seal as the eye is inflated following surgery and therefore requires no sutures for sealing. Accordingly, the probability of astigmatism is eliminated or greatly reduced and the reliance on sutures is eliminated.

29 Claims, 1 Drawing Sheet

METHOD OF MAKING SELF-SEALING EPISCLERAL INCISION

BACKGROUND OF THE INVENTION

This invention relates, in general, to surgery of the eye, and more particularly to a self-sealing episcleral incision useful in scleral tunnel surgery for the removal of cataracts and the implantation of artificial lenses.

It is well known to those in the opthalmology arts that microsurgery may be used to remove cataracts and implant artificial lenses to partially or wholly restore vision. Initially, a conjunctival incision is made to partially remove the conjunctiva and expose the limbus and sclera. The most conventional microscopic surgery method currently employed includes making an incision in either the limbus or the sclera directly posterior to the limbus. The incision is either linear or approximately follows the curvature of the limbus and extends into the anterior chamber directly in front of the iris.

A capsulrhexis is performed wherein a window is cut into the anterior of the crystalline lens capsule. Once the crystalline lens is opened, phacoemulsification is performed wherein the nucleus is removed using ultrasonic frequency and aspiration. The cortex is then removed by aspiration only. Once the nucleus and cortex have been removed, the empty lens capsule remains.

Following removal of lens material which includes the cataract, an artificial lens is implanted. The artificial lens is inserted through the incision, disposed in the empty lens capsule and stabilized therein. The artificial lens implant may be either a solid implant or a flexible folded implant. Both these types of implants are well known in the art. Once the lens implant has been successfully inserted into the lens capsule and stabilized, the incision is sealed with sutures so that the eye may be inflated.

A common problem with the described conventional microsurgery is suture induced astigmatism. The cornea is a potentially toric structure. The use of sutures in the limbus to seal the incision maximally alters the toricity of the cornea often creating an astigmatism which impairs vision. Additional suture induced complications include irritation of the eye, suture absesses, suture extrusion and foreign body reaction. Further, the fine sutures employed in opthalmic surgery are subject to breakage thereby exposing the wound to separation and dehiscence.

Scleral tunnel surgery greatly reduces the effect of sutures and suture induced astigmatism because the sutures are not disposed in the limbus, are much further away from the cornea and any material gathered by the sutures is sclera and not cornea. Standard scleral tunnel surgery includes making an incision in the sclera approximately 1 to 2 millimeters posterior to the limbus. This incision is also linear or approximately follows the curvature of the limbus. Following the scleral incision, a pocket or tunnel is formed through the sclera that extends into the anterior chamber of the eye.

Capsulrhexis, phacoemulsification and removal of the cortex to leave the empty lens capsule are performed in the same manner as described above. The artificial lens implant is inserted through the episcleral incision, transits the scleral tunnel and is properly positioned and stabilized in the empty lens capsule. The episcleral incision is then sealed with sutures and the eye inflated. Although the sutures sealing the scleral incision are not as detrimental as sutures disposed in the limbus, it is still possible for them to detrimentally effect the toricity of the cornea and cause an astigmatism.

In view of the above, it would be highly beneficial to have an episcleral incision that may be employed with scleral tunnel microsurgery that is substantially self-sealing, will admit solid or folded lens implants and greatly reduces or eliminates the probability of astigmatism.

SUMMARY OF THE INVENTION

Accordingly, it is an object of the present invention to provide an episcleral incision that is self-sealing.

Another object of the present invention is to provide a self-sealing episcleral incision that greatly reduces or eliminates the probability of astigmatism.

Another object of the present invention is to provide a self-sealing episcleral incision which does not rely on sutures for wound integrity.

Another object of the present invention is to provide a self-sealing episcleral incision having reduced incisional stress associated with lens implantation.

Another object of the present invention is to provide a self-sealing episcleral incision that will admit solid or folded lens implants of various sizes therethrough.

A further object of the present invention is to provide a self-sealing episcleral incision having a variable cord length.

The foregoing and other objects and advantages are achieved in the present invention by one embodiment in which, as a part thereof, includes a substantially self-sealing episcleral incision wherein the approximate central point of the incision is 1.5 to 3.0 millimeters posterior to the limbus. Portions of the incision extending from the approximate central point extend laterally away from the curvature of the limbus. The configuration of the self-sealing incision allows the incision to seal as the eye is inflated following surgery and therefore requires no sutures for sealing. Accordingly, the probability of astigmatism is eliminated or greatly reduced.

A more complete understanding of the present invention can be attained by considering the following detailed description in conjunction with the accompanying drawings.

DETAILED DESCRIPTION OF THE DRAWINGS

Figure 1:
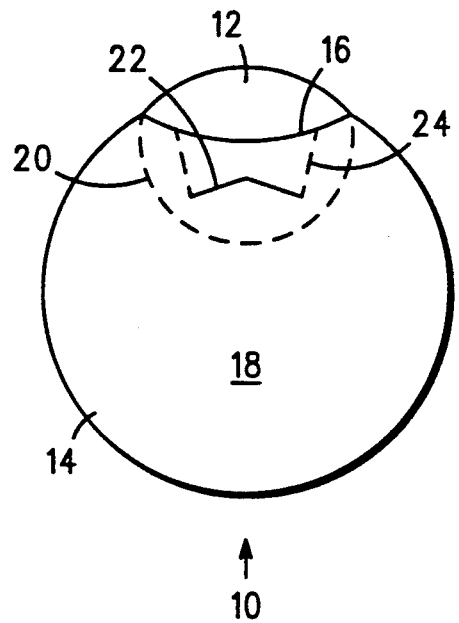
FIG. 1 is a schematic representation of a top view of a human eye.

FIG. 1 is a schematic representation of a top view of a human eye 10. Eye 10 includes the cornea 12 and the sclera 14. The limbus 16 is the top edge of cornea 12 where it encounters sclera 14. The conjunctiva 18 is the outer membrane which covers eye 10.

Microscopic scleral tunnel surgery is commonly used to remove cataracts and implant artificial lenses. To initiate scleral tunnel surgery, a conjunctival incision is made and conjunctiva 18 is partially removed to expose limbus 16 and sclera 14. The exposed area is represented by dotted lines 20. Once sclera 14 and limbus 16 have been exposed, an incision 22 is made in sclera 14. The approximate central point of incision 22 is 1.5 to 3.0 millimeters posterior to the limbus and most preferably, approximately 2.0 millimeters posterior to the limbus.

The depth of incision 22 is approximately 50 percent of the thickness of sclera 14 although it may be in the range of 25 to 75 percent of the thickness of sclera 14. Once incision 22 has been made to the desired depth, a scleral tunnel represented by dotted lines 24 is formed through sclera 14 at approximately the same depth as incision 22.

Figure 2:
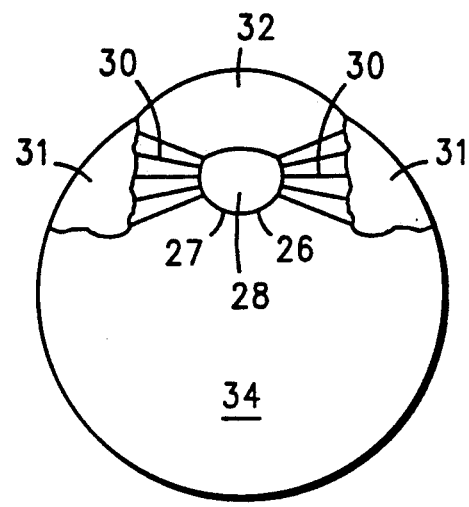
FIG. 2 is a schematic representation of the interior of a human eye.

FIG. 2 is a schematic representation of the interior of eye 10. The interior of eye 10 includes a crystalline lens 26. Crystalline lens 26 includes a lens capsule 27 and internal material 28 which includes a nucleus and cortex. Lens 26 is stabilized in eye 10 by zonular ligaments 30 and ciliary body 31. The anterior chamber 32 is the interior portion of eye 10 anterior to crystalline lens 26 and zonular ligaments 30. The posterior segment 34 is the interior portion of eye 10 posterior to crystalline lens 26 and zonular ligaments 30.

Now referring to FIGS. 1 and 2, scleral tunnel 24 extends into anterior chamber 32 of eye 10. Once anterior chamber 32 has been accessed by scleral tunnel 24, removal of internal material 28 of crystalline lens 26 which includes the cataract may begin. Initially, a capsulrhexis is performed wherein a window is cut into the anterior portion of lens capsule 27. Commonly, the window is oval and approximately 3.5 by 4.5 millimeters in size. Once the capsulrhexis has been performed, phacoemulsification is performed wherein the nucleus of crystalline lens 26 is removed with ultrasonic frequency and aspiration. Following the removal of the nucleus, the cortex of crystalline lens 26 is removed using only aspiration. Once the cortex has been removed, empty lens capsule 27 remains.

Following removal of internal material 28 of crystalline lens 26, an artificial lens is implanted. The artificial lens implant is inserted through incision 22, disposed in empty lens capsule 27 and stabilized therein. The artificial lens implant may be either a solid implant or a flexible folded implant, both of which are well known in the art. Once the lens implant has been successfully disposed in lens capsule 27 and stabilized, eye 10 is inflated initiating the self-sealing of incision 22.

Figure 3:
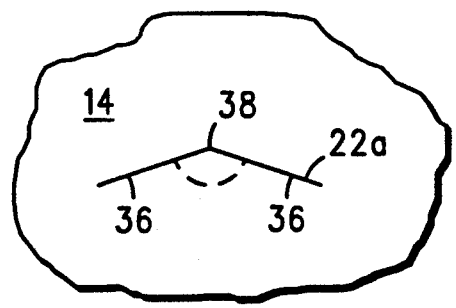
FIGS. 3-4 are highly enlarged representations of the configurations of incisions in accordance with the present invention.
Figure 4:
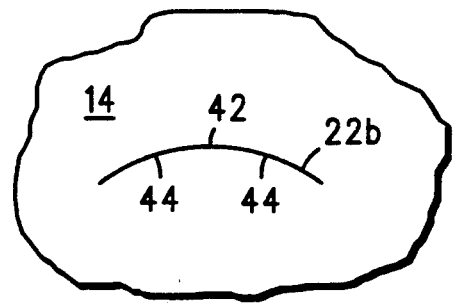

FIGS. 3 and 4 are highly enlarged representations of the configurations of incisions 22a and 22b, respectively, in accordance with the present invention. Incision 22a depicted in FIG. 3 includes two substantially linear portions 36 joining at an apex 38. Each linear portion is approximately 3 millimeters long in a preferred embodiment although the length can be varied to suit the size of the lens implant. An angle represented by dotted line 40 of approximately 120 degrees is between linear portions 36 in this embodiment. Angle 40 is preferred in a range of 100 to 160 degrees although an angle in the range of 80 to 175 degrees may be successfully employed.

As mentioned earlier, apex 38 is in the range of 1.5 to 3.0 millimeters posterior to limbus 16. Most preferably, apex 38 is approximately 2.0 millimeters posterior to limbus 16 and approximately at its 12 o'clock position. Further, linear portions 36 of incision 22a extend laterally away from the curvature of limbus 16.

Now referring to incision 22b depicted by FIG. 4. Incision 22b is of a curvilinear configuration and includes an approximate central point 42. Approximate central point 42 is 1.5 to 3.0 millimeters posterior to limbus 16. Most preferably, approximate central point 42 is approximately 2.0 millimeters posterior to limbus 16 and approximately at its 12 o'clock position. Incision 22b further includes lateral portions 44 extending from approximate central point 42 and laterally away from the curvature of limbus 16.

The configurations of incisions 22a and 22b have many advantages over the configurations of conventional incisions employed for scleral tunnel surgery. The configurations wherein linear portions 36 of incision 22a and lateral portions 44 of incision 22b extend laterally away from the curvature of limbus 16 enable incisions 22a and 22b to be substantially self-sealing. When eye 10 is inflated following surgery, the force vectors acting on incisions 22a and 22b induce the closure of scleral tunnel 24 so that incisions 22a and 22b become water-tight and require no sutures for sealing.

The present invention has many advantages associated with it due to its self-sealing properties and absence of dependence on sutures. First, there are no sutures to affect the toricity of cornea 12 and therefore, suture induced astigmatism is eliminated. Second, common problems associated with sutures such as eye irritation, suture abesses, suture extrusion and foreign body reaction are also eliminated. Third, because there are no sutures that may break, the wound will not be exposed to separation and dehiscence. Finally, surgical emergencies such as expulsive hemorrhage and choroidal hemorrhage are spontaneously controlled because incision 22 will self-seal prior to the loss of intraocular contents.

The configurations of incisions 22a and 22b have reduced incision stresses associated therewith. The configurations allow incisions 22a and 22b to be stretched without tearing. This allows incision 22 to have a variable cord length capable of admitting solid or folded lens implants therethrough. One of skill in the art will understand that the cord length is the linear distance between the ends of incision 22. For example, a solid ovoid biconvex lens implant having dimensions of 5 millimeters by 6 millimeters may be successfully inserted into an incision 22 having a cord length of 3.5 millimeters without tearing incision 22. Further, even larger lens implants of up to 6 millimeters in diameter may be inserted through larger incisions 22 although a single suture may occasionally be required for complete sealing. It should be understood that scleral tunnel 24 will probably have to be wider than the cord length of incision 22 where it encounters anterior chamber 32.

Thus it is apparent that there has been provided, in accordance with the invention, an improved episcleral incision which meets the objects and advantages set forth above. While specific embodiments of the invention have been shown and described, further modifications and improvements will occur to those skilled in the art. It is desired that it be understood, therefore, that this invention is not limited to the particular forms shown and it is intended in appended claims to cover all modifications which do not depart from spirit and scope of this invention.

What is claimed is:

1. A method of making a substantially self-sealing episcleral incision comprising;
   providing incision making means;
   making an incision in the sclera with said means; and
   said incision having an appropriate central point 1.5 to 3.0 millimeters posterior to the limbus wherein portions of said incision extend away from said approximate central point and extend laterally away from the curvature of said limbus.

2. The method of claim 1 further including making an incision having a depth in the range of 25 to 75 percent of the thickness of the sclera.

3. The method of claim 2 further including making an incision having a depth of approximately 50 percent of the thickness of the sclera.

4. The method of claim 1 further including making an incision having the approximate central point approximately 2.0 millimeters posterior to the limbus.

5. The method of claim 1 further including making an incision having the approximate central point posterior to the approximate 12 o'clock position of the limbus.

6. The method of claim 1 further including making an incision having variable cord length.

7. The method of claim 1 further including making an incision having a curvilinear configuration.

8. The method of claim 1 further including making an incision having two substantially linear portions joining at the approximate central point of said incision.

9. A method of making a substantially self-sealing episcleral incision comprising:
providing incision making means;
making an incision in the sclera with said means; and
said incision comprising two substantially linear portions joining at an apex 1.5 to 3.0 millimeters posterior to the limbus, said linear portions extending from said apex laterally away from the curvature of said limbus and further, said linear portions having an angle in the range of 80 to 175 degrees therebetween.

10. The method of claim 9 further including making an incision having a depth in the range of 25 to 75 percent of the thickness of the sclera.

11. The method of claim 10 further including making an incision having a depth of approximately 2.0 millimeters posterior of the limbus.

12. The method of claim 9 further including making an incision having the apex approximately 2.0 millimeters posterior to the limbus.

13. The method of claim 9 further including making an incision having the apex posterior to the approximate 12 o'clock position of the limbus.

14. The method of claim 9 further including making an incision having variable cord length.

15. The method of claim 9 further including making an incision having an angle in the range of 100 to 160 degrees between the linear portions.

16. The method of claim 15 further including making an incision having an angle of approximately 120 degrees between the linear portions.

17. The method of claim 9 further including making a scleral tunnel from said incision extending into the anterior chamber of the eye.

18. The method of claim 17 further including making a scleral tunnel wherein the width of said scleral tunnel where it encounters the anterior chamber is greater than the cord length of the incision.

19. A method of making a substantially self-sealing episcleral incision comprising:
providing incision making means;
making an incision in the sclera with said means; and
said incision having two substantially linear portions of approximately 3.0 millimeters in length, said linear portions joining at an apex approximately 2.0 millimeters posterior to the approximate 12 o'clock position of the limbus, said linear portions having an angle therebetween of approximately 120 degrees and extending from said apex laterally away from the curvature of said limbus, said incision having a depth of approximately 50 percent of the thickness of the sclera.

20. The method of claim 19 further including making a scleral tunnel extending from the incision to the anterior chamber of the eye.

21. The method of claim 20 further including making a scleral tunnel wherein the width of said scleral tunnel where it encounters the anterior chamber is greater than the cord length of the incision.

22. A method of making a substantially self-sealing episcleral incision comprising:
providing incision making means;
making an incision in the sclera with said means; and
said incision having a curvilinear configuration and an approximate central point 1.5 to 3.0 millimeters posterior to the limbus, portions of said incision extending from said approximate central point further extending laterally away from the curvature of said limbus.

23. The method of claim 22 further including making an incision having a depth in the range of 25 to 75 percent of the thickness of the sclera.

24. The method of claim 23 further including making an incision having a depth approximately 50 percent of the thickness of the sclera.

25. The method of claim 24 further including making an incision having the approximate central point approximately 2.0 millimeters posterior to the limbus.

26. The method of claim 22 further including making an incision having the approximate central point posterior to the approximate 12 o'clock position of the limbus.

27. The method of claim 22 further including making an incision having variable cord length.

28. The method of claim 22 further including forming a scleral tunnel from the incision extending to the anterior chamber of the eye.

29. The method of claim 28 further including forming a scleral tunnel wherein the width of said scleral tunnel where it encounters the anterior chamber is greater than the cord length of the incision.

* * * * *